United States Patent [19]

Ho et al.

[11] 4,296,251

[45] Oct. 20, 1981

[54] SYNTHESIS OF (+)-CIS-HOMOCARONIC ACID

[75] Inventors: T. L. Ho; Zia U. Din; Carlos G. Cardenas, all of Jacksonville, Fla.

[73] Assignee: SCM Corporation, New York, N.Y.

[21] Appl. No.: 150,197

[22] Filed: May 15, 1980

[51] Int. Cl.$^3$ .............................................. C07C 51/34
[52] U.S. Cl. ................................................. 562/506
[58] Field of Search ..................................... 562/506

[56] References Cited

U.S. PATENT DOCUMENTS

| | | | |
|---|---|---|---|
| 3,637,826 | 1/1972 | Berg | 562/506 |
| 3,708,528 | 1/1973 | Mukherjee | 562/506 |
| 4,222,964 | 9/1980 | Berkel | 562/506 |

FOREIGN PATENT DOCUMENTS 43-22592  9/1968  Japan .................................. 562/506

OTHER PUBLICATIONS

Matsui, Agr., Biol., Chem., 29 pp. 784–786 (1965).
Matsui, Agr., Biol., Chem., 31 pp. 33–39 (1967).
Welch, J. Org., Chem., 42 pp. 2108–2111 (1977).

Primary Examiner—Natalie Trousof
Assistant Examiner—Michael Shippen
Attorney, Agent, or Firm—Robert A. Sturges; Merton H. Douthitt

[57] ABSTRACT

A process for producing (+)-cis-homocaronic acid from 2-caren-4-ol, 2-caren-4-one, 3-caren-2-ol, or mixtures thereof is disclosed. The reactants are ozonized, the ozonides produced are treated with an oxidizing agent, and the (+)-cis-homocaronic acid is recovered. The oxidizing agent can be hydrogen peroxide in either a basic or an acid medium.

7 Claims, No Drawings

SYNTHESIS OF (+)-CIS-HOMOCARONIC ACID

BACKGROUND OF THE INVENTION

The present invention relates to a process for producing (+)-cis-homocaronic acid in surprisingly high yields from 2-caren-4-ol, 2-caren-4-one, 3-caren-2-ol, or mixtures thereof. The process consists of ozonizing the reactants to form the ozonides and then oxidizing the ozonides to yield (+)-cis-homocaronic acid. The (+)-cis-homocaronic acid is an important synthetic intermediate for producing (+)-trans-chrysanthemic acid. Natural and synthetic pyrethroid insecticides may then be made using the (+)-trans-chrysanthemic acid as an essential constituent.

One previously proposed procedure for synthesizing (+)-cis-homocaronic acid is described in U.S. Pat. No. 3,565,915 issued to Matsui, et al. However, the reactant 2-caren-4-one oxime, obtained from 3-carene, is used as the starting material. This oxime is oxidized with potassium permanganate to obtain the desired optically active (+)-cis-homocaronic acid. However, the Matsui patent notes that the production of (+)-cis-homocaronic acid by the oxime is hindered by the "exceedingly low yield".

One advantage of the present inventive process is that the yields obtained therefrom are much higher than from previously proposed processes. In fact, the theoretical yields from the present invention are in excess of 90%. The yields are high enough so that the process may economically be practiced on an industrial scale. Additionally, ozonization of the starting reactants involves a less expensive and more easily controlled method to produce the desired (+)-cis-homocaronic acid than use of potassium permanganate suggested in the Matsui patent above.

SUMMARY OF THE INVENTION

One aspect of this invention is a process for producing (+)-cis-homocaronic acid from 2-caren-4-ol, 2-caren-4-one, 3-caren-2-ol, or mixtures thereof comprising the steps of ozonizing the reactants, treating the ozonides produced with an oxidizing agent, and recovering (+)-cis-homocaronic acid. Another aspect of this invention is the use of hydrogen peroxide in either a basic or an acid medium as the oxidizing agent in the inventive process.

DETAILED DESCRIPTION OF THE INVENTION

The present invention is conveniently illustrated by using as a starting reactant either pure 2-caren-4-ol, 2-caren-4-one, or 3-caren-2-ol. However, the process also is able to utilize a mixture of any of the above as a starting material. Additionally, the stereochemical configuration of the starting carenol's hydroxy group may be either cis or trans to the 3-member ring. A diastereomeric mixture of the epimeric carenols or a pure cis- or trans-carenol will all lead to the same desired (+)-cis-homocaronic acid product when processed in accordance with the present invention. The starting reactants are ozonized and then the ozonides are treated with an oxidizing agent. The desired (+)-cis-homocaronic acid is recovered, usually by extraction with ether.

The three starting reactants have the following structures:

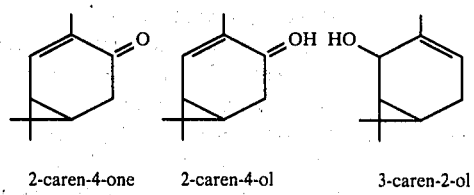

2-caren-4-one     2-caren-4-ol     3-caren-2-ol

The proportions of each of the above compounds in any reaction mixture do not affect the yields. Therefore, the reaction mixture proportions are a matter of convenience.

Ozonizing the reaction mixture is best carried out at low temperatures. Preferably this temperature will be below 0° C., most preferably much below 0° C. Therefore, the starting reactant compound or mixture should be cooled to a low temperature before being treated with ozone. The ozonide derived from 2-caren-4-one most plausibly has the following structure:

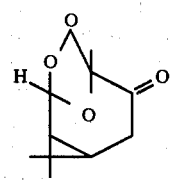

The ozonization is complete when an excess of ozone is detected in the reaction mixture. Ozonization is best carried out at reduced temperatures because the desired ozonides are unstable at room temperature.

Following the formation of the ozonides, the oxidizing agent is added and the mixture is allowed to come to room temperature, 25° C., while being stirred. The most common oxidizing agent used is hydrogen peroxide. The hydrogen peroxide can be added either in a basic medium such as aqueous sodium hydroxide or in an acidic medium such as formic acid. Since this reaction is slightly exothermic, cooling may be required to control the reaction. The reaction temperature must not be allowed to exceed 50°–70° C. Excessive temperature of the reaction may lead to violent decomposition.

Recovery of the optically active (+)-cis-homocaronic acid is accomplished by extraction. The solvent is first distilled off under reduced pressure and the residue is dissolved in water. Ether or hydrocarbon solvents are most conveniently used to remove any neutral products when the oxidation after ozonization is carried out in a basic medium. After this washing, the aqueous phase is acidified and then extracted with an organic solvent such as methylene chloride. The final yields are often in the range of 95 to 100%. These high yields make the process economical for use on an industrial scale.

The following examples are intended to illustrate the invention and should not be construed as limiting the claims. The indicated temperatures are in degrees Celsius.

EXAMPLE 1

A solution containing 2 gms. of 2-caren-4-one (75% pure) was dissolved in 25 mls. of methanol. This starting reaction mixture was subjected to ozonization at a temperature of −78° C. The solution was first placed in a reaction vessel and cooled by a dry ice bath. Ozone was bubbled through the reaction mixture until ozone was detected in the exit gases by an iodide test. Excess ozone was expelled by a stream of oxygen and the reaction mixture was then stirred while 5 mls. of water were added. Following the water, 3 mls. of 50% hydrogen peroxide were added and the reaction mixture was then allowed to come to room temperature, 25° C. After reaching room temperature, the reaction mixture was then stirred for 5 hours. Next, 3 gms. of sodium hydroxide in 6 mls. of water were added slowly drop by drop. The slightly exothermic reaction was cooled by placing the reaction vessel in an ice bath. Continuing the reaction at a temperature of around 25° C., the mixture was stirred for 18 hours.

To recover the desired (+)-cis-homocaronic acid, the methanol was first removed under reduced pressure at 40° C. The residue was next dissolved in water and then was extracted with ether to remove any neutral products formed during the above reaction. The aqueous portion of the extraction was then acidified with 40 ml. of 9% hydrochloric acid saturated with sodium chloride. The acidified aqueous solution was extracted four times again with ether. Magnesium sulfate was introduced into the combined ether extracts in order to eliminate any remaining water. The solvent was then removed from the dried extract by distillation. The final yield of (+)-cis-homocaronic acid was 1.7 g. in the form of crystalline white solid. This represented a yield of 98%, calculated on the theoretical yield basis.

EXAMPLE 2

A solution containing 1.6 g. of 2-caren-4-ol and 0.4 g. of 2-caren-4-one in 50 mls. of methanol was prepared. This solution was then reacted according to the procedure set out in Example 1, including using the same amounts of hydrogen peroxide, etc. The yield was 2.25 g. of (+)-cis-homocaronic acid again appearing as a crystalline white solid. This represented a yield of 99%, calculated on the theoretical yield basis.

What is claimed is:

1. A process for producing (+)-cis-homocaronic acid from 2-caren-4-ol, 2-caren-4-one, 3-caren-2-ol, or mixtures thereof comprising the steps of:
   ozonizing the reactants,
   treating the ozonides produced with, hydrogen peroxide and
   recovering (+)-cis-homocaronic acid.
2. The process of claim 1 wherein said oxidizing agent is hydrogen peroxide in a basic medium.
3. The process of claim 2 wherein said basic medium is aqueous sodium hydroxide.
4. The process of claim 1 wherein said oxidizing agent is hydrogen peroxide in an acid medium.
5. The process of claim 4 wherein said acid medium is formic acid.
6. The process of claim 1 wherein said reactants are cooled to a temperature below 0° C. before ozonizing.
7. The process of claim 6 wherein said reactants are cooled to a temperature of −78° C. before ozonizing.

* * * * *